(12) United States Patent
Maev et al.

(10) Patent No.: US 9,897,680 B2
(45) Date of Patent: Feb. 20, 2018

(54) ULTRASOUND BONE PHANTOM MATERIAL COMPATIBLE WITH MRI

(71) Applicant: TRUE PHANTOM SOLUTIONS INC., Windsor (CA)

(72) Inventors: Roman Gr. Maev, Windsor (CA); Adrian Pawel Wydra, Windsor (CA); Emil Strumban, West Bloomfied, MI (US)

(73) Assignee: TRUE PHANTOM SOLUTIONS INC., Windsor (CA)

( * ) Notice: Subject to any disclaimer, the term of this patent is extended or adjusted under 35 U.S.C. 154(b) by 0 days.

(21) Appl. No.: 15/166,404

(22) Filed: May 27, 2016

(65) Prior Publication Data

US 2017/0003371 A1    Jan. 5, 2017

Related U.S. Application Data

(60) Provisional application No. 62/166,922, filed on May 27, 2015.

(51) Int. Cl.

| | |
|---|---|
| *C08F 2/46* | (2006.01) |
| *C08F 2/50* | (2006.01) |
| *C08G 61/04* | (2006.01) |
| *G01R 33/58* | (2006.01) |
| *A61B 8/00* | (2006.01) |
| *C08K 3/00* | (2018.01) |
| *C08K 3/22* | (2006.01) |
| *G01R 33/48* | (2006.01) |
| *A61B 8/08* | (2006.01) |
| *G01N 29/30* | (2006.01) |
| *G09B 23/28* | (2006.01) |

(52) U.S. Cl.
CPC ............ *G01R 33/58* (2013.01); *A61B 8/0875* (2013.01); *A61B 8/587* (2013.01); *C08K 3/0033* (2013.01); *C08K 3/22* (2013.01); *G01N 29/30* (2013.01); *G01R 33/4814* (2013.01); *G09B 23/28* (2013.01); *C08K 2003/2227* (2013.01)

(58) Field of Classification Search
CPC .. G01R 33/58; G01R 33/4814; C08K 3/0033; C08K 2003/2227; C08K 3/22; A61B 8/587; A61B 8/857; G09B 23/28

USPC ................ 522/81, 71, 189, 184, 1; 520/1
See application file for complete search history.

(56) References Cited

U.S. PATENT DOCUMENTS

2011/0098380 A1* 4/2011 Hearn .................. C07C 37/20
                                                              523/400

OTHER PUBLICATIONS

Hartsgrove et al, Simulated Biolgical Materials for Elecromagnetic Radiation Absorption Studies, 1987, Bioelectromagnetics 8: 29-36.*
Tatarinov et al, Modeling the influence of mineral content and porosity onultrasound parameters in bone by using synthetic phantoms, 1999, Mechanics of Composite Materials, vol. 35, No. 2.*
Shellock, Magnetic Resonance Procedures: Health Effects and Safety, Speicial Edition, Dec. 26, 2000, CRC Press,p. 396.*
US Composites, 2001, Epoxy Resin and Hardener Systems, http://www.uscomposites.com/epoxy.html, pp. 1-2.*
Wydra, Development of a new forming process to fabricate a wide range of phantoms that highly match the acoustical properties of human bone, 2013, Electronic Theses and Dissertations paper 4937 University of Windsor, pp. 1-138.*
A J Clarke et al., "A phantom for quantitative ultrasound of trabecular bone", Phys. Med. Biol. 39 (1994) 1677-1687.
A. Tatarinov et al., "Modeling the Influence of Mineral Content and Porosity on Ultrasound Parameters in Bone by Using Synthetic Phantoms", Mechanics of Composite Materials, vol. 35, No. 2, 1999.
R. Stretitzki et al., "The Influence of Porosity and Pore Size on the Ultrasonic Properties of Bone Investigated Using a Phantom Material", Osteoporos Int (1997) 7:370-375.
Keith A. Wear, "Ultrasonic attenuation in parallel-nylon-wire cancellous-bone-mimicking phantoms", J. Acoust. Soc. Am., vol. 124, No. 6, Dec. 2008, pp. 4042-4046.

* cited by examiner

*Primary Examiner* — Jessica Whiteley
(74) *Attorney, Agent, or Firm* — Carlson, Gaskey & Olds, P.C.

(57) ABSTRACT

A method of fabricating ultrasound bone phantom material compatible with magnetic resonance imaging (MRI) is provided. The bone phantom material has ultrasound and physical parameters that are characteristic of human cortical and trabecular bones, and is well suited for the fabrication of bone phantoms intended for the development and testing of ultrasound medical diagnostic imaging techniques as well as high-intensity focused ultrasound (HIFU) therapy methods and other MRI imaging applications.

17 Claims, 2 Drawing Sheets

ULTRASOUND BONE PHANTOM MATERIAL COMPATIBLE WITH MRI

RELATED APPLICATIONS

This application claims the benefit of U.S. Provisional Application No. 62/166,922, filed May 27, 2015, the entirety of which is herein incorporated by reference.

BACKGROUND

Traditionally, phantoms that closely mimic the physical properties of various human tissues have been very important for the development and testing of medical imaging modalities. Ideally, the material of the phantom should perfectly mirror the qualities of the bone being studied. For example, bone-mimicking phantom materials for use in ultrasound should have the same ranges of speeds of sound, attenuation coefficients, and backscatter coefficients as real bone. These parameters should be controllable in the manufacturing process of the phantom material, and their variation within the range of room temperatures should be small.

Speeds of sound in human bones vary over a fairly small range with an average value of about 3000 m/s. The amplitude of attenuation coefficients vary over the range from 2 dB/cm to about 4 dB/cm at a frequency of 1 MHz. The bones of the human skeleton can be divided into two types: cortical bone (around 80% of the total skeleton), and cancellous, or trabecular, bone (around 20% of the total skeleton). The latter has a porous structure made up of cortical trabecules, the pores being filled with bone marrow. Cortical bone has a homogenous, compact structure, being less than 10% porous. Trabecular bone has a much more complex composite structure.

The size, shape and concentration of pores vary between skeletal sites; the proportion by volume which is marrow is known as the porosity. Trabecular bone has a higher porosity, 50-90%, which makes its modulus and ultimate compressive strength around 20 times inferior than that of cortical bone. Hence, there is a requirement for the bone phantom material to be able to mimic porosity in a controllable way and allow it to imitate healthy and osteoporotic bones. Therefore, both the cortical and trabecular bone properties are very challenging to mimic, especially if in addition to ultrasound properties MRI compatibility is required, as in the case of HIFU therapy and anatomical MRI imaging methods. Making the ultrasound bone phantom material MRI compatible would considerably expand its applications for the development of ultrasound-based imaging diagnostic and therapeutic techniques. Currently there are no such ultrasound bone phantom materials available.

SUMMARY

One Disclosed herein is an ultrasound bone phantom material compatible with MRI and a method of preparation thereof, in which the velocity of sound, ultrasonic attenuation, bulk density and porosity can be advantageously controlled and the affinity of the ultrasound bone phantom material to real bone can be advantageously held.

An ultrasound bone phantom material compatible with MRI is accomplished through resin-based composites fabricated by molding or 3D printing. Accordingly, disclosed herein is a method for producing an ultrasound bone phantom material compatible with MRI by mixing of a resin binder, a resin hardener, a solid filler and optionally a catalyst for promoting reaction between the resin binder and the resin hardener. A ceramic powder is used as a solid filler to make an ultrasound cortical bone phantom material. The ceramic powder is mixed with inorganic or organic particulate material to make an ultrasound trabecular bone phantom material.

The ultrasound bone phantom material is compatible with MRI and can be manufactured at room temperature, wherein the background matrix can accept solid fillers of low melting temperature.

The ultrasound bone phantom material is compatible with MRI and its acceptability to solid fillers provides flexibility and a wide range of choice in solid fillers for the purpose of adjusting the sonic properties and porosity of the ultrasound bone phantom material compatible with MRI as desired.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention.

DETAILED DESCRIPTION

Figure 1:
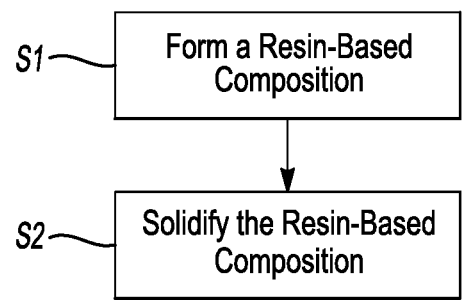
FIG. 1 is a flow chart showing a method of preparing an ultrasound bone phantom material.

The ultrasound bone phantom material according to one example includes: (1) a resin binder (in turn containing a resin, a hardener and a catalyst), (2) one or more density control ceramic powder materials and (3) one or more porosity control particulate materials.

The resin constituent may be any type of epoxy resin, urethane resin, acrylic resin, phenolic resin, UV cured resin (i.e. useful in molding compositions or 3D printing). Non-limiting examples of suitable epoxy resins include epichlorohydrin derived liquid epoxy resin, phenolic novolac epoxy resin, biphenyl epoxy resin, hydroquinone epoxy resin, stilbene epoxy resin, and mixtures and combinations thereof. Epoxy cresol novolac resin is suitable for use in some embodiments. The epoxy resins may be used either individually or as a mixture of two or more resins. A preferred epichlorohydrin derived liquid epoxy resin is commercially available from Momentive Industries, Ltd. of USA, but other resins could be used.

A resin hardener constituent is provided for promoting crosslinking of the molding composition to form a polymer composition. Non-limiting examples of suitable hardeners include diethylenetriamine aliphatic polyamine hardener, cresol novolac hardener, dicyclopentadiene phenol hardener, limonene type hardener, anhydrides, and mixtures thereof. Diethylenetriamine aliphatic polyamine hardener is particularly desirable. Also, in a similar manner as with the epoxy resins, the resin hardener may be used either individually or as a mixture of two or more hardeners.

A preferred diethylenetriamine aliphatic polyamine hardener is commercially available from Momentive Industries Ltd. of USA, but other hardeners can be used.

A ceramic powder component is provided to control the density in the bone phantom material. To adjust the density of bone phantom material, a mixture of submicron and micron-scale and ceramic powders is used. Non-limiting examples of ceramic powders which could be used include alumina, zirconia, silicon carbide, boron nitride and mixtures and combinations thereof. A preferred alumina ceramic powder is commercially available from, e.g., Kramer Industries, Inc. (Piscataway, N.J., USA).

An inorganic or organic particulate component is provided to control the porosity of the bone phantom material. Non-limiting examples of inorganic and organic granular component which could be used include poppy seeds, hemp seeds, polyurethane particles, silicone particles, gelatin, hydrogel particles and mixture of thereof. A preferred particular material is hemp seeds or poppy seeds commercially available from any Canadian grocery store.

A catalyst is provided for promoting reaction between the epoxy resin and the resin hardener during curing of the bone phantom material molding composition. Incorporating a catalyst directly in the resin-ceramic composite provides effective catalytic activity for subsequent reaction, since both the epoxy resin and the hardener are present within the composite structure.

Examples of such catalysts include, but are not limited to, basic and acidic catalysts such as metal halide Lewis acids, including boron trifluoride, stannic chloride, zinc chloride and the like;

As will be described in more detail herein, the resin, the resin hardener, the ceramic powder and the particulate material are mixed to form a resin-based composite, from which ultrasound cortical bone phantom material of low, medium and high density and ultrasound trabecular bone phantom material of low, medium and high porosity can be fabricated. The amount of resin provided in the resin-based composition may range from about 10 weight percent to about 40 weight percent based on the weight of the resin-based composite, desirably for medium density cortical bone phantom from about 15 weight percent to about 20 weight percent based on the weight of the resin-based composite. The amount of resin hardener in the resin-based composite may range from about 5 weight percent to about 30 weight percent based on the weight of the resin-based composite, desirably for medium density cortical bone phantom from about 7 weight percent to about 15 weight percent based on the weight of the resin-based composite. The ceramic powder may be provided in the resin-based composite at a range of about 50 weight percent to about 90 weight percent based on the weight of the resin-based composite, more desirably for medium density cortical bone phantom at a range of about 70 weight percent to about 80 weight percent based on the weight of the resin-based composite. A mixture of submicron and micron-scale and ceramic powders is used with a weight ratio from 1:20 to 1:30. In embodiments in which a catalyst is included within the epoxy-clay nanocomposite, the amount of catalyst provided in the resin-based composite ranges from about 1.0 weight percent to about 40 weight percent based on the weight of the resin-based composite, desirably for medium density cortical bone phantom from about 0.5 weight percent to about 5.0 weight percent based on the weight of the resin-based composite.

In case of trabecular bone phantom material, the resin-based composite is further provided with organic or inorganic particulate material component to form the resin-based composition. The particulate material component may include different known organic and inorganic materials. For example, the particulate material may be poppy seeds, hemp seeds, polyurethane particles, silicone particles, hydrogel particles, gelatin, and mixtures thereof. In one particular example, the particulate material components are hemp seeds.

The amount of the particular material component in the resin-based composition ranges from about 5 weight percent to about 70 weight percent based on the total weight of the resin-based composition (that allows to vary porosity between 5% and 70%), desirably for medium porosity trabecular bone phantom from about 20 weight percent to about 50 weight percent based on the total weight of the resin-based composition.

Figure 2:
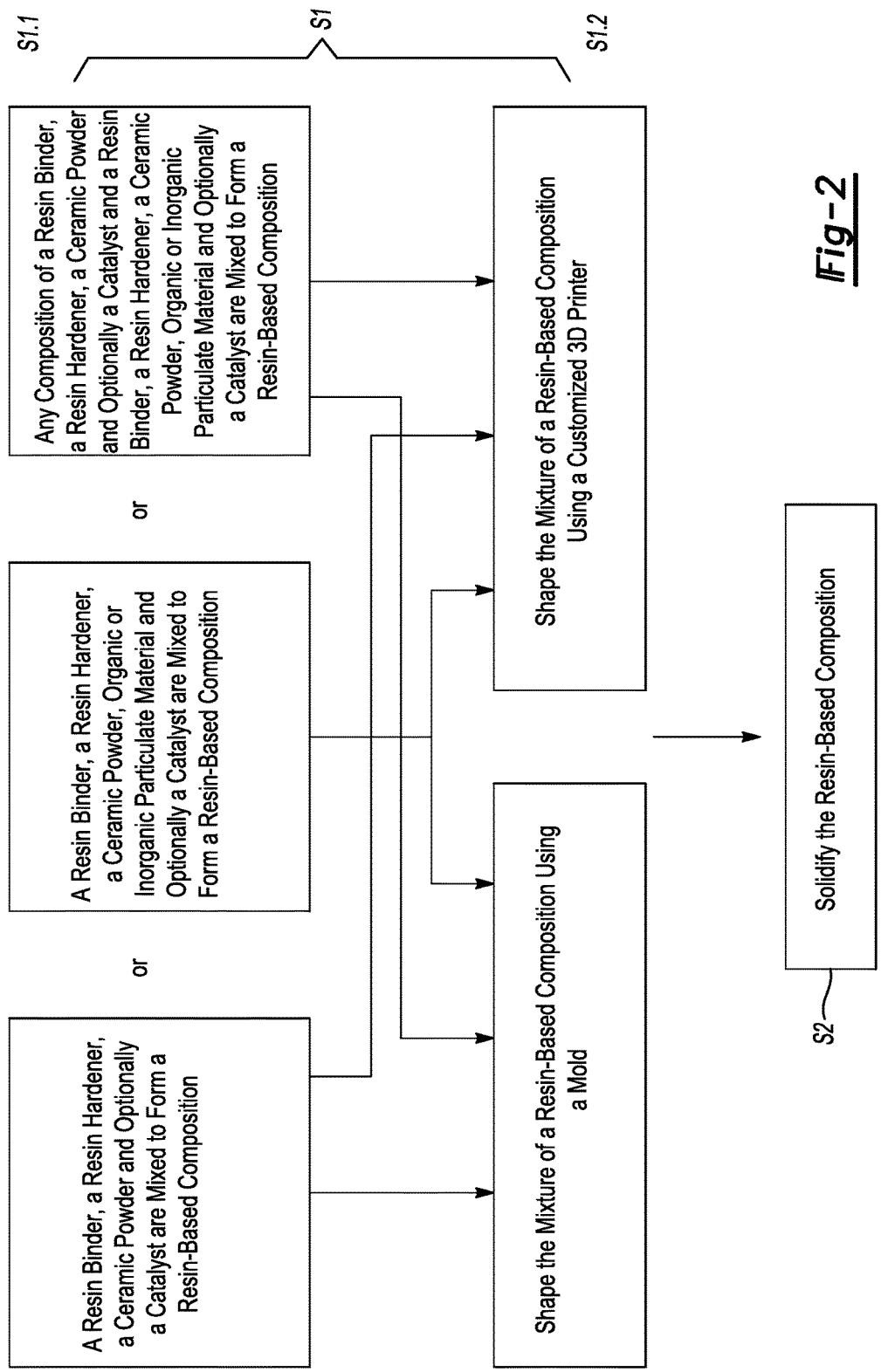
FIG. 2 is a detailed flow chart showing a method of preparing the non-porous and porous bio-material.

FIG. 1 is a flow chart showing a method of preparing an ultrasonic bone phantom material compatible with MRI. Referring to FIG. 1, the method of preparing ultrasonic bone phantom material includes the following steps. First, in step S1, a body of a resin-based cortical bone phantom composition is formed by mixing a resin, a resin hardener, ceramic powders and a catalyst or a body of a resin-based trabecular bone phantom composition is formed by mixing a resin, a resin hardener, ceramic powders, organic and inorganic particular materials and a catalyst. Then, in step S2, the body of a resin-based cortical bone phantom composition is solidified to obtain the ultrasound cortical bone phantom compatible with MRI or the body of a resin-based cortical bone phantom composition is solidified to obtain the ultrasound trabecular bone phantom compatible with MRI. FIG. 2 is a detailed flow chart showing a method of preparing the ultrasound bone phantom compatible with MRI. As shown in FIG. 2, the step S1 may include steps S1.1 and S1.2. In the step S1.1, a resin, a resin hardener, ceramic powders and a catalyst are mixed together to form a resin-based composition. In the step S1.2, the resin-based composition is shaped into the body of a resin-based composition using a mold. That is, the mixture is poured into the mold to form the body, which has the shape of a bone in skeleton. The mold may be removed after or before the body is dried. It is to be noted that the step of shaping the mixture by the mold is not essential, and it is also possible to cut a small block from the dried body or to machine the small block. Alternatively the mixture can be loaded to a customized 3D printer and directly 3D printed to the desired shape.

Figure 3:
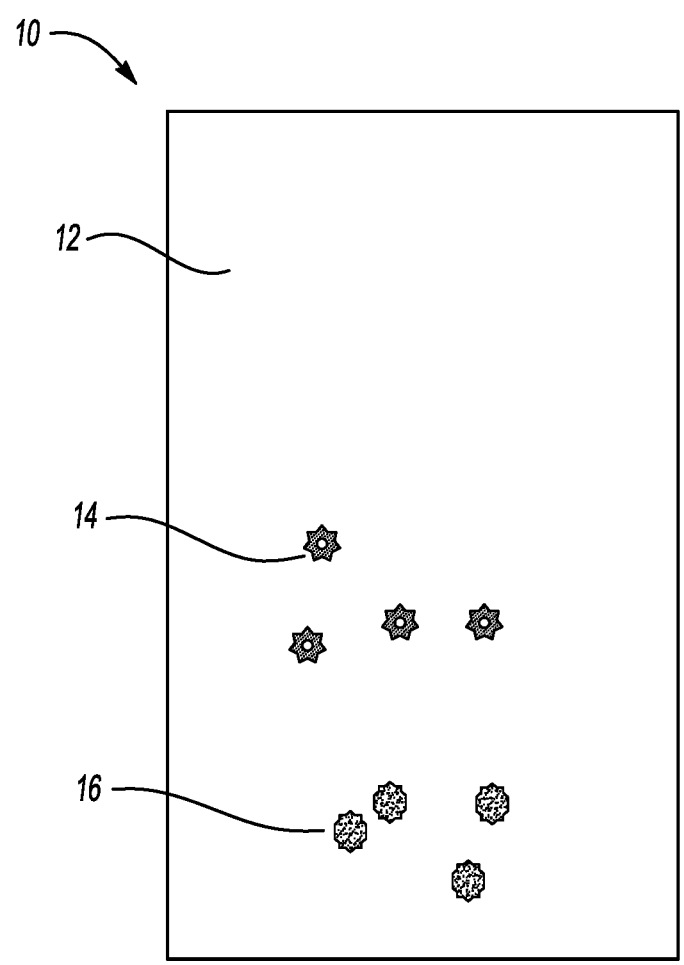
FIG. 3 is a schematic of an example ultrasound bone phantom.

FIG. 3 schematically shows an ultrasonic bone phantom 10 including a resin binder 12 and one or more density control materials 14. Optionally, there may also be one or more porosity control particulate materials 16. Again, the phantom 10 could be formed in any shape (in a mold or via additive manufacturing, for example). The phantom 10 can be formed as cortical bone, trabecular bone or as layers of each, with areas of varying density and porosity. This can be done by combining different mixtures in different parts of the mold. Alternatively, varying these properties in different parts of the phantom could be done in a fairly straightforward manner using additive manufacturing (e.g. 3D printers).

In the following example, the method of preparing the porous bio-material will be described to prove that the method is simple and the ultrasonic bone phantom material compatible with MRI has excellent properties.

EXAMPLES

Example 1

This example represents a comparative example demonstrating an ultrasound cortical bone phantom composition of medium density including resin component, hardener component, catalyst component and ceramic powder component (Table 1). First the resin was uniformly pre-mixed with hardener and catalyst (see Table 1) for 1 to 2 minutes in a conventional blender and then the ceramic powder is added to the mixture was stirred for another 1 to 2 minutes. The formed ultrasound cortical bone molding composition was transferred into a mold, left for drying for about 16 hours at 21° C. and then heated in the oven for 2 hours at 93° C.

TABLE 1

| COMPONENT | WEIGHT PERCENT |
|---|---|
| 1. Resin[1] | 15 |
| 2. Hardener[2] | 8 |
| 3. Catalyst[3] | 1 |
| 4. ALUMINA (44/+10 MICRONS) | 75 |
| 5. ALUMINA (SUB-MICRON) | 1 |
| Total: | 100 |

[1]Epon 828
[2]Epicure 3055
[3]3-glycidoxypropyltrimethoxysilane

Example 2

This example represents a comparative example demonstrating three different types of ultrasound cortical bone phantoms, their compositions and ultrasound properties (Table 2). The ultrasound cortical bone phantom molding composition was prepared as in Example 1, including the resin component, hardener component and ceramic powder component.

TABLE 2

| | COMPONENT | | | | PROPERTIES | | |
|---|---|---|---|---|---|---|---|
| Phantom Type | Resin Epon | Hardener Epikure | Alumina Powder (44/+10 microns) | Alumina Powder (Sub-Microns) | Sound Velocity | Ultrasonic Attenuation at 1 MHz | Density |
| Low Density | 20 g | 10 g | 75 g | 1.0 g | 2700 m/s | 4 dB/cm | 2.15 g/cm$^3$ |
| Medium Density | 20 g | 10 g | 90 g | 1.2 g | 2900 m/s | 3 dB/cm | 2.25 g/cm$^3$ |
| High Density | 20 g | 10 g | 105 g | 1.4 g | 3100 m/s | 3 dB/cm | 2.35 g/cm$^3$ |

Example 3

This example represents a comparative example demonstrating three different types of trabecular bone phantoms, their compositions and ultrasound properties (Table 3). The molding composition "Medium Density Bone Material" was prepared as in Example 1, but then hemp seeds-a particular material component was added to the mixture and stirred for 1 to 2 minutes.

TABLE 3

| | COMPONENT | | PROPERTIES | | |
|---|---|---|---|---|---|
| Phantom Type | Medium Density Bone Material | Hemp Seeds | Sound Velocity | Ultrasonic Attenuation at 1 MHz | Density |
| Low Porosity Trabecular bone | 20 g | 10 g | 2400 m/s | 30 dB/cm | 1.86 |
| Medium Porosity Trabecular Bone | 20 g | 20 g | 2000 m/s | 36 dB/cm | 1.68 |
| High Porosity Trabecular Bone | 20 g | 30 g | 1600 m/s | 41 dB/cm | 1.43 |

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. An ultrasound bone phantom material compatible with MRI comprising:
   a) a blended mixture resin binder including a resin and a resin hardener;
   b) a diamagnetic micron-scale solid filler component; and
   c) a diamagnetic submicron solid filler component.

2. The ultrasound bone phantom material as in claim 1, wherein the resin binder is between about 10 percent to about 40 percent of a total weight of the ultrasound bone phantom material.

3. The ultrasound bone phantom material as in claim 2, wherein the resin hardener is between about 5 percent to about 30 percent of a total weight of the ultrasound bone phantom material.

4. The ultrasound bone phantom material as in claim 1, wherein said resin is a liquid epoxy resin.

5. The ultrasound bone phantom material as in claim 4, wherein said resin is an epichlorohydrin-derived liquid epoxy resin.

6. The ultrasound bone phantom material as in claim 1, wherein said resin hardener is selected from the group consisting of diethylenetriamine aliphatic polyamine, phenol novolacs, cresol novolacs, anhydrides, and mixtures thereof.

7. The ultrasound bone phantom material as in claim 1, wherein said resin is capable of being hardened by a UV light.

8. The ultrasound bone phantom material as in claim 1, wherein the amount of said solid filler component in said ultrasound bone phantom material ranges from about 50 weight percent to about 90 weight percent based on the total weight of the ultrasound bone phantom material.

9. The ultrasound bone phantom material as in claim 1, wherein the micron-scale filler component and the submicron filler component in said ultrasound bone phantom material ceramic powder with a weight ratio of 1:20 to 1:30.

10. The ultrasound bone phantom material as in claim 1, wherein said filler component is alumina.

11. The ultrasound bone phantom material as in claim 1, wherein said ultrasound bone phantom material further comprises a catalyst for promoting reaction between the resin and the hardener.

12. The ultrasound bone phantom material as in claim 1, wherein the material is compatible with MRI.

13. The ultrasound bone phantom material as in claim 12, wherein the simulated porosity in the ultrasound bone phantom material is between 5% and 70%.

14. The ultrasound bone phantom material as in claim 13, wherein an average size of pores in the ultrasound bone phantom material is greater than 100 microns.

15. The ultrasound bone phantom material as in claim 14 wherein a cortical portion is formed to represent cortical bone and a trabecular portion is formed to represent trabecular bone, wherein the cortical portion has different porosity from the trabecular portion.

16. The ultrasound bone phantom material as in claim 1, wherein said micron-scale solid filler component and said submicron filler component is selected from the group consisting of alumina, zirconia, silicon carbide, boron nitride, and mixtures and combinations thereof.

17. An ultrasound bone phantom material compatible with MRI comprising:
a) a blended mixture resin binder including a resin and a resin hardener;
b) a micron-scale solid filler component selected from the group consisting of alumina, zirconia, silicon carbide, boron nitride, and mixtures and combinations thereof; and
c) a submicron solid filler component selected from the group consisting of alumina, zirconia, silicon carbide, boron nitride, and mixtures and combinations thereof.

* * * * *

UNITED STATES PATENT AND TRADEMARK OFFICE
CERTIFICATE OF CORRECTION

| | |
|---|---|
| PATENT NO. | : 9,897,680 B2 |
| APPLICATION NO. | : 15/166404 |
| DATED | : February 20, 2018 |
| INVENTOR(S) | : Roman Gr. Maev, Adrian Pawel Wydra and Emil Strumban |

It is certified that error appears in the above-identified patent and that said Letters Patent is hereby corrected as shown below:

In the Claims

In Claim 9, Column 7, Line 12; replace "material ceramic powder" with --material comprises ceramic powder--

In Claim 16, Column 8, Line 11; replace "component is" with --component are--

Signed and Sealed this
First Day of February, 2022

Drew Hirshfeld
*Performing the Functions and Duties of the*
*Under Secretary of Commerce for Intellectual Property and*
*Director of the United States Patent and Trademark Office*